US011344218B2

(12) United States Patent
Senegas et al.

(10) Patent No.: US 11,344,218 B2
(45) Date of Patent: May 31, 2022

(54) MR FINGERPRINTING FOR DETERMINING PERFORMANCE DEGRADATION OF THE MR SYSTEM

(71) Applicant: KONINKLIJKE PHILIPS N.V., Eindhoven (NL)

(72) Inventors: Julien Senegas, Eindhoven (NL); Daniel Wirtz, Eindhoven (NL); Sascha Krueger, Eindhoven (NL); Vincent Jeanne, Eindhoven (NL); Thirukumaran Thangaraj Kanagasabapathi, Eindhoven (NL); Joerg Sabczynski, Eindhoven (NL); Peter Forthmann, Eindhoven (NL)

(73) Assignee: Koninklijke Philips N.V., Eindhoven (NL)

( * ) Notice: Subject to any disclaimer, the term of this patent is extended or adjusted under 35 U.S.C. 154(b) by 1160 days.

(21) Appl. No.: 15/546,310

(22) PCT Filed: Jan. 14, 2016

(86) PCT No.: PCT/EP2016/050588
§ 371 (c)(1),
(2) Date: Jul. 26, 2017

(87) PCT Pub. No.: WO2016/120073
PCT Pub. Date: Aug. 4, 2016

(65) Prior Publication Data
US 2018/0014745 A1    Jan. 18, 2018

Related U.S. Application Data

(60) Provisional application No. 62/109,085, filed on Jan. 29, 2015.

(30) Foreign Application Priority Data

Feb. 26, 2015  (EP) .................................. 15156732

(51) Int. Cl.
*A61B 5/055* (2006.01)
*A61B 5/00* (2006.01)
(Continued)

(52) U.S. Cl.
CPC ............ *A61B 5/055* (2013.01); *A61B 5/0037* (2013.01); *A61B 5/0077* (2013.01);
(Continued)

(58) Field of Classification Search
CPC ..... A61B 5/0037; A61B 5/0077; A61B 5/055; A61B 5/1079; A61B 5/1128;
(Continued)

(56) References Cited

U.S. PATENT DOCUMENTS

2002/0118280 A1    8/2002  Medlar et al.
2010/0002071 A1*   1/2010  Ahiska .................. H04N 5/217
                                                         348/36
(Continued)

FOREIGN PATENT DOCUMENTS

GB         2418495 A      3/2006
WO      1999027839 A2     6/1999
(Continued)

*Primary Examiner* — Pascal M Bui Pho
*Assistant Examiner* — Alexei Bykhovski

(57) ABSTRACT

A contact-free method of determining biometric parameters and physiological parameters of a subject of interest (20) to be examined by a medical imaging modality (10), comprising steps of taking (72) a picture by a first digital camera (52) including a total view of an examination table (44); applying (74) a computer vision algorithm or an image processing algorithm to the picture for determining a biometric parameter of the subject of interest (20) in relation to the examination table (44); taking (78) at least one picture with a second digital camera (58), whose field of view (60) includes a region of the subject of interest (20) that is related (Continued)

to the at least one determined biometric parameter; using data indicative of the determined biometric parameter to identify (82) a subset of pixels of the at least one picture taken by the second digital camera (58) that define a region of interest (64) from which at least one physiological parameter of the subject of interest (20) is to be determined, taking (84) a plurality of pictures of the region of the subject of interest (20) with the second digital camera (58), and applying (86) a computer vision algorithm or an image processing algorithm to pictures of the plurality of pictures taken by the second digital camera (58) for calculating the region of interest (64) in the pictures of the plurality of pictures for determining the physiological parameter of the subject of interest (20) during examination; a camera system (50) for determining, in a contact-free way, biometric parameters and physiological parameters of a subject of interest (20) to be examined by use of a medical imaging modality (10) and using such method; and—a medical imaging modality (10) configured for acquisition of scanning data of at least a portion of a subject of interest (20), the medical imaging modality (10) comprising such camera system.

20 Claims, 2 Drawing Sheets

(51) Int. Cl.
*A61B 5/107* (2006.01)
*A61B 5/11* (2006.01)
*G01R 33/28* (2006.01)
*G01R 33/32* (2006.01)
*G01R 33/54* (2006.01)
*G06T 7/00* (2017.01)
*A61B 6/00* (2006.01)
*A61B 5/113* (2006.01)

(52) U.S. Cl.
CPC .......... *A61B 5/1079* (2013.01); *A61B 5/1128* (2013.01); *A61B 5/1135* (2013.01); *A61B 6/527* (2013.01); *A61B 6/547* (2013.01); *G01R 33/283* (2013.01); *G01R 33/32* (2013.01); *G01R 33/546* (2013.01); *G06T 7/0012* (2013.01); *G06T 2207/10088* (2013.01)

(58) Field of Classification Search
CPC ....... A61B 5/1135; A61B 6/527; A61B 6/547; G01R 33/283; G01R 33/32; G01R 33/546; G06T 2207/10088; G06T 7/0012
See application file for complete search history.

(56) References Cited

U.S. PATENT DOCUMENTS

| | | | |
|---|---|---|---|
| 2013/0035588 A1 | 2/2013 | Shea et al. | |
| 2013/0281818 A1 | 10/2013 | Vija et al. | |
| 2013/0342851 A1 | 12/2013 | Dresel et al. | |
| 2015/0087997 A1* | 3/2015 | Haider | A61B 5/0077 600/474 |

FOREIGN PATENT DOCUMENTS

| | | |
|---|---|---|
| WO | 2005030330 A1 | 4/2005 |
| WO | 2009050589 A2 | 4/2010 |

* cited by examiner

MR FINGERPRINTING FOR DETERMINING PERFORMANCE DEGRADATION OF THE MR SYSTEM

CROSS REFERENCE TO RELATED APPLICATIONS

This application is a U.S. national phase application of International Application No. PCT/EP2016/050588, filed on Jan. 14, 2016, which claims the benefit of U.S. provisional Application Serial No. 62/109,085 filed on Jan. 29, 2015 and EP application Serial No. 15156732.8 filed Feb. 26, 2015, each of which is incorporated herein by reference.

FIELD OF THE INVENTION

The invention pertains to a contact-free method of determining biometric parameters and physiological parameters of a subject of interest to be examined by a medical imaging modality, a camera system for determining, in a contact-free way, biometric parameters and physiological parameters of the subject of interest to be examined by use of the medical imaging modality and a medical imaging modality, in particular a magnetic resonance imaging system or a computer tomography imaging system, comprising such camera system.

BACKGROUND OF THE INVENTION

In the field of medical scanning it is known that a plurality of biometric parameters related to a subject of interest to be examined, usually a patient, has to be determined and permanently tied to the prospected scanning data. This is usually carried out by an orderly or other medical staff member by manually entering the plurality of biometric parameters into a data system. Typical biometric parameters would include a weight, posture (supine, prone, left-cubitus, right-cubitus) and orientation (head-first, feet-first) of the subject of interest on an examination table.

In addition, physiological parameters often need to be determined during scanning examination. Typical physiological parameters would include a cardiac or a respiratory waveform of the subject interest.

SUMMARY OF THE INVENTION

Manual input of biometric parameters into a data system is prone to human error. In many cases, default biometric parameters are used, as it would be too complex or too time-consuming to determine them for an individual patient. Determining physiological parameters during scanning examination is usually performed by means of suitable sensors requiring setting up on the subject of interest. For instance, one conventional way of determining a respiratory waveform of the subject of interest is by employing a respiration belt-type monitoring device which includes a respiration sensor that usually is attached to the thorax of the subject of interest, and is held by a belt wound around the thorax.

It is therefore an object of the invention to provide a contact-free method of determining biometric parameters and physiological parameters of a subject of interest to be examined by a medical imaging modality, not requiring any set up time related to the individual subject of interest, and that it a suitable embodiment can be carried out in an automatic manner.

In one aspect of the present invention, the object is achieved by a contact-free method of determining biometric parameters and physiological parameters of a subject of interest to be examined by a medical imaging modality. The medical imaging modality comprises an examination space for arranging the subject of interest within for examination purposes, and an examination table having an upper surface for supporting the subject of interest prior and after the examination outside the examination space as well as while being arranged inside the examination space during examination.

The phrase "biometric parameter", as used in this application, shall be understood particularly as a mechanical measure characterizing at least a portion of an individual subject of interest, and shall in particular encompass anthropometric parameters such as, but not limited to, distances between characteristic natural landmarks of the subject of interest.

The phrase "physiological parameter", as used in this application, shall be understood particularly as a physical measure characterizing the function of at least a portion of an individual subject of interest, and shall in particular encompass parameters such as, but not limited to, respiration cycle parameters and cardiac cycle parameters.

The method comprises steps of
- prior to arranging the subject of interest within the examination space, taking at least one picture with a first digital camera, wherein the field of view of the first digital camera includes a total view of the upper surface of the examination table,
- applying at least one out of a computer vision algorithm and an image processing algorithm to the at least one picture taken by the first digital camera for determining at least one biometric parameter of the subject of interest in relation to the upper surface of the examination table,
- taking at least one picture with a second digital camera, whose field of view includes a region of the subject of interest that is related to the at least one determined biometric parameter,
- using data that are at least indicative of the at least one determined biometric parameter of the subject of interest to identify a subset of pixels of the at least one picture taken by the second digital camera that define a region of interest from which at least one physiological parameter of the subject of interest is to be determined,
- taking a plurality of pictures of the region of the subject of interest with the second digital camera, and
- applying at least one out of a computer vision algorithm and an image processing algorithm to pictures of the plurality of pictures taken by the second digital camera for calculating the region of interest in the pictures of the plurality of pictures for determining the at least one physiological parameter of the subject of interest during examination.

The phrase "in relation to the upper surface of the examination table", as used in this application, shall be understood particularly to encompass data that are indicative of at least one out of an orientation of the at least one biometric parameter relative to a characteristic feature of the upper surface of the examination table or a distance of the at least one biometric parameter relative to the characteristic feature of the upper surface of the examination table. Furthermore, data shall be encompassed that are indicative of spatial coordinates of the at least one biometric parameter relative to the examination table. If the position of the upper surface (or a table top, respectively) of the examining table is being recorded, as is the case in many medical scanning modalities, the at least one biometric parameter of the subject of interest would thus also be determined in relation to the medical scanning modality.

The phrase "total view" of the upper surface, as used in this application, shall be understood particularly such that the view comprises a portion of at least 30% of a length of each edge of the upper surface of the examination table, more preferable at least 40%, and, most preferable, at least 50% of the length of each edge of the upper surface of the examination table.

The phrase "computer vision algorithm and image processing algorithm", as used in this application, shall be understood particularly to include any of the methods of 2D and 3D analysis of 2D or 3D images, such as, but not limited to the methods described in standard textbooks such as Richard Szeliski, *Computer Vision: Algorithms and Applications, Springer*, 2010, ISBN 978-1848829343.

The first digital camera and the second digital camera may each be one out of a single-shot camera or a video camera. The spectral sensitivity of the cameras may include electromagnetic radiation in a range encompassing the optical regime of electromagnetic waves visible to human beings, and/or the regime of near UV (380-200 nm wavelength, NUV), infrared radiation (Near Infrared (NIR), Mid Infrared (MIR) and Far Infrared (FIR)) and/or the regime of radio frequency radiation of extremely high frequency (EHF), i.e. a frequency bandwidth reaching from visible light down to radio frequencies as low as 30 GHz.

As another option, the method may include a step of illuminating the region of the subject of interest with an emitting source whose spectrum of emitted electromagnetic radiation is adapted to the spectral sensitivity of the camera.

One advantage of the method lies in that the biometric parameters and physiological parameters of the subject of interest are determined in a contact-free manner.

Moreover, the method enables to determine physiological parameters at exactly the region of the subject of interest, without any further effort of adjustment that is related to the biometric parameter that has been determined from a previously taken picture.

Another advantage lies in that the determining of the biometric and physiological parameters does not, besides a general set up time for installing an appropriate apparatus, require any additional set up time that is related to the individual subject of interest the parameters are determined at. This can result in a reduced total examination time.

In a preferred embodiment, the step of taking a plurality of pictures of the region of the subject of interest with the second digital camera and the step of applying at least one out of a computer vision algorithm and an image processing algorithm to the pictures of the plurality of pictures taken by the second digital camera for calculating the region of interest in the pictures of the plurality of pictures for determining the at least one physiological parameter of the subject of interest is semi-automatically or automatically carried out during examination.

The phrase "semi-automatically", as used in this application, shall be understood particularly as being executed in an automatic manner upon activation, either by a human being or by a time or trigger signal.

In this way, the at least one physiological parameter of the subject of interest can be determined during examination reproducibly, reliably, and in a way that is not prone to human error.

In another preferred embodiment, the step of taking at least one picture with the first digital camera includes obtaining at least one picture that is formed as a depth image including depth data and that is taken by a digital range camera.

Preferably, the range camera is designed as one out of a time-of-flight camera or a range camera based on structured light technology.

In one embodiment, the range camera includes a photonic mixer device (PMD) with a plurality of image elements formed by pixels.

In one embodiment, the range camera is designed as a 3-D laser scanning device that performs a distance measurement at every pointing direction.

As is commonly known, depth images, also known as depth maps, depict depth variations in an imaged scene. A depth image includes optical image data and depth values assigned to image points, for instance formed by pixels, of the optical image.

In this way, biometric parameters can precisely be determined also for configurations in which portions of the subject interest extend upwardly from the upper surface of the examination table.

In yet another preferred embodiment, the method further comprises a step of determining a plurality of parameters of a deformable human body model representing the subject of interest by applying a numerical fitting procedure to the data of the depth image. The plurality of parameters of the deformable human body model may comprise biometric parameters as well as parameters that are independent from determined biometric parameters.

In this way, the position and orientation of the subject of interest relative to the upper surface of the examination table can be determined as a whole, which can be used in support of identifying the region of interest from which the at least one physiological parameter of the subject of interest is to be determined.

In one embodiment, the step of taking a plurality of pictures with the second digital camera comprises taking a plurality of depth images. In this way, physiological parameters such as a respiratory cycle can readily be determined from the variance of depth information in the depth images.

In another preferred embodiment, the method further comprises steps of taking a plurality of pictures by at least one out of the first digital camera and the second digital camera while the subject of interest is being arranged within the examination space, applying at least one out of a computer vision algorithm and an image processing algorithm to pictures of the plurality of pictures for tracking positions of the examination table, using data that are indicative of the tracked positions of the examination table and at least a subset of the data that are indicative of the at least one biometric parameter of the subject of interest in relation to the upper surface of the examination table for determining a position of the region of interest.

In this way, a spatial correlation between the at least one biometric parameter and the region of interest can readily be determined.

In one embodiment, the data to be transferred to the second digital camera that are indicative of the position of the examination table are provided by a table control unit of the medical imaging modality. In this case, a suitable data link, either by wire or wireless, between the table control unit and the second digital camera has to be provided.

In one embodiment, the step of determining at least one biometric parameter of the subject of interest in relation to the upper surface of the examination table includes determining at least one out of an exact position and an orientation of the region of the subject of interest of which a plurality of pictures are to be taken by the second digital camera, relative to the upper surface of the examination table.

By that, the step of defining the region of interest can be supported and accelerated.

In another aspect of the invention, a camera system is provided for determining, in a contact-free way, biometric parameters and physiological parameters of a subject of interest to be examined by use of a medical imaging modality. The medical imaging modality includes an examination space for arranging the subject of interest within during examination and an examination table having an upper surface for supporting the subject of interest prior and after the examination outside the examination space as well as while being arranged inside the examination space during examination.

The camera system comprises a first digital camera that is arranged in an entrance region of the medical imaging modality, and is configured for taking at least one picture prior to arranging the subject of interest within the examination space, wherein the field of view of the first digital camera includes a total view of the upper surface of the examination table. The phrase "entrance region", as used in this application, shall be understood particularly as a volume that the subject of interest has to traverse before entering the examination space.

The camera system further comprises a second digital camera, which is configured to take pictures of at least a region of the subject of interest while the subject of interest is being arranged within the examination space during examination.

Moreover, the camera system includes a camera system control unit having at least one digital memory unit and at least one processor unit, and a data link, connecting the camera system control unit, the first digital camera and the second digital camera for enabling data transmission.

The camera system control unit is configured
  to apply at least one out of a computer vision algorithm and an image processing algorithm to the at least one picture taken by the first digital camera, for determining at least one biometric parameter of the subject of interest in relation to the upper surface of the examination table,
  to take at least one picture with the second digital camera, whose field of view includes a region of the subject of interest that is related to the at least one determined biometric parameter,
  to use data that are at least indicative of the at least one determined biometric parameter of the subject of interest to identify a subset of pixels of the at least one picture taken by the second digital camera that define a region of interest from which at least one physiological parameter of the subject of interest is to be determined,
  to take a plurality of pictures, by the second digital camera, of a region of the subject of interest that is related to the at least one determined biometric parameter; and
  to retrieve data from the second digital camera that represent pictures of the plurality of pictures taken by the second digital camera, and to apply at least one out of a computer vision algorithm and an image processing algorithm to calculate the region of interest in the pictures of the plurality of pictures for determining the at least one physiological parameter of the subject of interest during examination.

The camera system control unit may be a separate unit especially assigned to the camera system. Alternatively, the tasks of the camera system control unit may instead at least partially be executed by a control unit of the medical imaging modality.

With a suitable embodiment of such a camera system, any embodiment of the contact-free method of determining biometric parameters and physiological parameters of a subject of interest to be examined by a medical imaging modality described herein can be carried out.

Data transmission may be mutually enabled between any pair formed by the camera system control unit, the first digital camera and the second digital camera. Data transmission may alternatively be enabled only between the camera system control unit and the first digital camera and between the camera system control unit and the second digital camera.

In a preferred embodiment of the camera system, the camera system control unit is an integral part of either the first digital camera or the second digital camera. This configuration would have the additional benefit of saving parts and costs.

In another preferred embodiment of the camera system, at least one of the first digital camera and the second digital camera is a range camera. Most preferably, both the first digit camera and the second digital camera are designed as range cameras, providing the advantages described before with regard to an embodiment of the method in accordance with the invention.

It is another aspect of the invention to provide a medical imaging modality that is configured for acquisition of scanning data of at least a portion of a subject of interest. The medical imaging modality comprises a scanning unit having an examination space provided for arranging at least the portion of the subject of interest within. Adjacent to the examination space, the medical imaging modality has an entrance region that the subject of interest has to traverse to enter the examination space for examination.

The medical imaging modality further comprises a control unit configured for controlling functions of the medical imaging modality, and a signal processing unit configured to generate scanning images from the acquired scanning data.

Furthermore, the medical imaging modality includes an embodiment of the camera system disclosed herein.

In a preferred embodiment of the medical imaging modality, the first digital camera is arranged in an upper portion of the entrance region of the medical imaging modality, with a lens of the first digital camera being directed substantially downwards.

In yet another embodiment, the medical imaging modality is formed as a magnetic resonance imaging system that is configured for acquiring magnetic resonance images of at least a portion of a subject of interest. The scanning data are formed by magnetic resonance signals and the generated scanning images are formed by magnetic resonance images.

The scanning unit of the magnetic resonance imaging system further includes
  a main magnet provided for generating a static magnetic field $B_0$ at least in the examination space, wherein the examination space is provided in a bore region of the main magnet,
  a magnetic gradient coil system configured for generating gradient magnetic fields superimposed to the static magnetic field $B_0$, at least one radio frequency antenna device that is configured for applying a radio frequency excitation field $B_1$ to nuclei of or within the portion of the subject of interest for magnetic resonance excitation, and at least one radio frequency antenna device that is configured for receiving magnetic resonance signals from the nuclei of or within the portion of the subject of interest that have been excited by applying the radio frequency excitation field $B_1$.

It will be readily appreciated by those skilled in the art that the camera system disclosed herein is also applicable to other medical imaging modalities. In particular, the medical imaging modality may be designed as a computer tomography (CT) device, a Positron Emission Tomography (PET) device or a combined PET/CT device.

With regard to further technical features and advantages of the disclosed method, reference is explicitly made herewith to the description related to the camera system, the figures and their corresponding figure captions, and vice versa.

BRIEF DESCRIPTION OF THE DRAWINGS

These and other aspects of the invention will be apparent from and elucidated with reference to the embodiments described hereinafter. Such embodiment does not necessarily represent the full scope of the invention, however, and reference is made therefore to the claims and herein for interpreting the scope of the invention.

In the drawings.

DETAILED DESCRIPTION OF EMBODIMENTS

Figure 1:
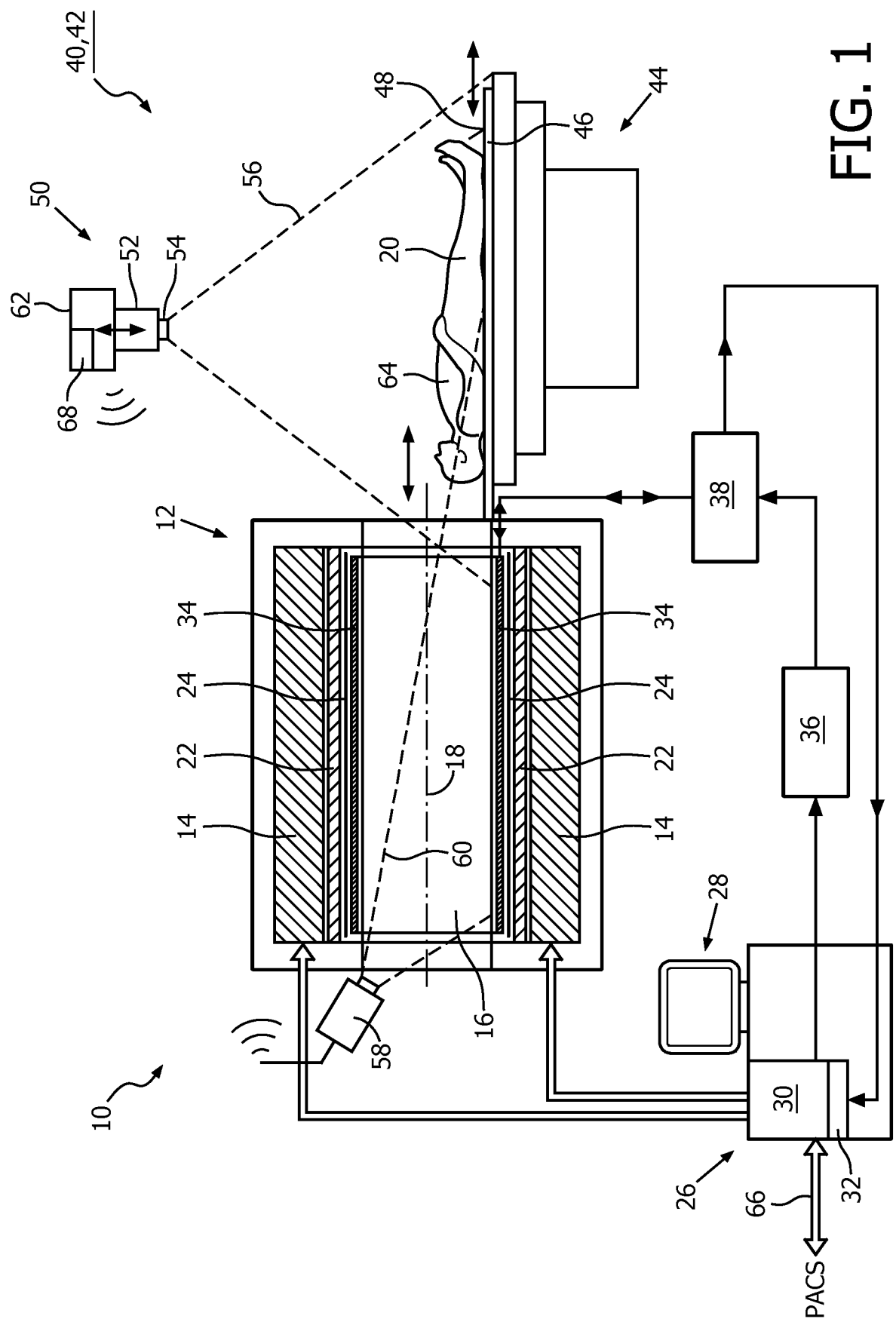
FIG. 1 shows a schematic illustration of a part of an embodiment of medical imaging modality in accordance with the invention, designed as a magnetic resonance imaging system.
Figure 2:
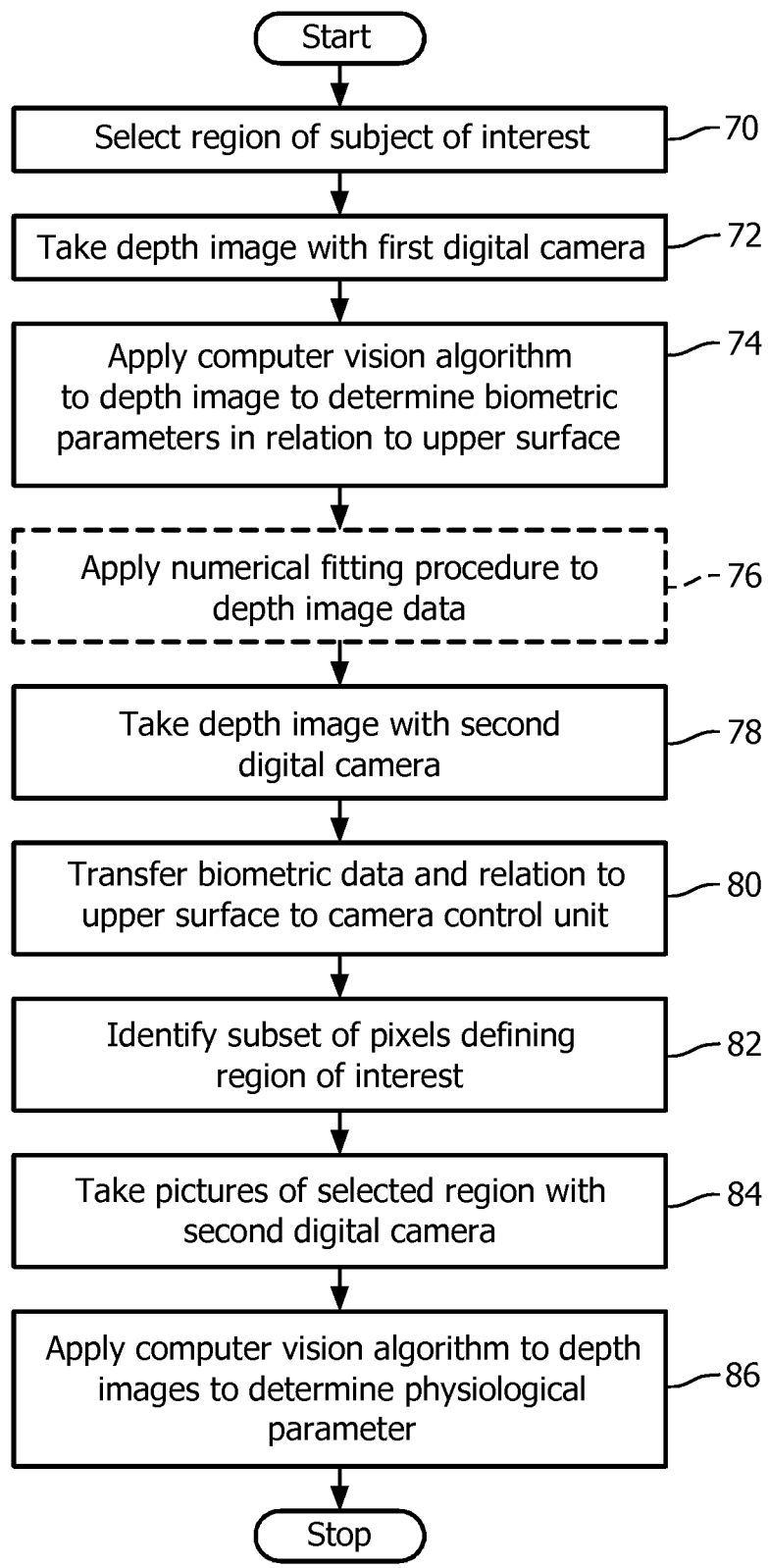
FIG. 2 shows a flow chart of an embodiment of the method in accordance with the invention.

FIG. 1 shows a schematic illustration of a part of an embodiment of a medical imaging modality 10 in accordance with the invention that is configured for acquisition of scanning data of at least a portion of a subject of interest 20, usually a patient. The medical imaging modality 10 is designed, without limitation for the scope of protection, as a magnetic resonance imaging system. A camera system 50, as described for this embodiment of the medical imaging modality 10, is also applicable to other medical imaging modalities, such as positron emission tomography devices or computer tomography devices, as will be appreciated to those skilled in the art.

Acquired scanning data are formed by magnetic resonance signals and generated scanning images are formed by magnetic resonance images.

The magnetic resonance imaging system is thus configured for acquisition of magnetic resonance images of at least a portion of the subject of interest 20. To this end, the magnetic resonance imaging system comprises a scanning unit 12 with a main magnet 14 provided for generating a static magnetic field $B_0$. The main magnet 14 has a central bore that provides an examination space 16 around a center axis 18 for the subject of interest 20 to be positioned within. The static magnetic field $B_0$ is generated by the main magnet 14 at least in the examination space 16. The static magnetic field $B_0$ defines an axial direction of the examination space 16, aligned in parallel to the center axis 18.

Adjacent to the central bore, the magnetic resonance imaging system has an entrance region 40 that the subject of interest 20 has to traverse to enter the examination space 16, usually head first. The magnetic resonance imaging system comprises an examination table 44 having a slidably arranged table top 46 with an upper surface 48 for supporting the subject of interest 20 prior and after an examination outside the examination space 16 as well as while being arranged inside the examination space 16 during the examination. As indicated in FIG. 1, the subject of interest 20 is lying in dorsal position on the upper surface 48 for entering the examination space 16. However, it is also contemplated that the subject of interest 20 may as well be lying on the examination table 44 in other positions, for instance in a prone or a lateral position.

The magnetic resonance imaging system further comprises a magnetic gradient coil system 22 with magnetic gradient coils provided for generating gradient magnetic fields superimposed to the static magnetic field $B_0$. The magnetic gradient coils are concentrically arranged within the bore of the main magnet 14, as is known in the art.

Further, the magnetic resonance imaging system includes a radio frequency antenna device 34 designed as a whole-body coil that is provided for applying a radio frequency magnetic field to the examination space 16 during radio frequency transmit phases to excite nuclei of or within the subject of interest 20. The radio frequency antenna device 34 is also configured for receiving magnetic resonance signals during radio frequency receive phases from the nuclei of or within the portion of the subject of interest 20 that have been excited by applying the radio frequency excitation field $B_1$. In an operational state of the magnetic resonance imaging system, radio frequency transmit phases and radio frequency receive phases are taking place in a consecutive manner. The radio frequency antenna device 34 is arranged concentrically within the bore of the main magnet 14. As is well known in the art, a cylindrical metal radio frequency shield 24 is arranged concentrically between the magnetic gradient coils of the magnetic gradient coil system 22 and the radio frequency antenna device 34.

The magnetic resonance imaging system further comprises a control unit 26 provided for controlling functions of the magnetic resonance imaging system. The control unit 26 comprises a human interface device for displaying and controlling purposes that is designed as a touch screen device 28.

Furthermore, the magnetic resonance imaging system includes a radio frequency transmitter unit 36 that is connected to and controlled by the control unit 26. The radio frequency transmitter unit 36 is provided to feed radio frequency power of a magnetic resonance radio frequency to the radio frequency antenna device 34 via a radio frequency switching unit 38 during the radio frequency transmit phases. During radio frequency receive phases, the radio frequency switching unit 38 directs the magnetic resonance signals from the radio frequency antenna device 34 to a signal processing unit 30 residing in the control unit 26. The signal processing unit 30 is configured for processing acquired magnetic resonance signals to generate scanning images represented by magnetic resonance images of the portion of the subject of interest 20 from the acquired scanning data represented by the magnetic resonance signals. This technique is well known to those skilled in the art and thus need not be described in further detail herein.

The control unit 26 further comprises a digital memory unit 32 for at least temporarily storing the generated magnetic resonance images. The magnetic resonance imaging system is connected to a Picture Archiving and Communication System (PACS) of the medical center that it is installed in via a data connection 66. In this way, data can be transferred between the magnetic resonance imaging system and the PACS.

Moreover, the magnetic resonance imaging system includes a camera system 50 for determining, in a contact-free way, biometric parameters and physiological parameters of the subject of interest 20 to be examined by use of the magnetic resonance imaging system.

The camera system 50 comprises a first digital camera 52 that is designed as an autofocus range camera of the time-of-flight type, including a photonic mixer device (PMD) with a plurality of image elements formed by pixels.

The first digital camera 52 is arranged in an upper portion 42 of the entrance region 40 of the magnetic resonance imaging system, and is configured for taking at least one picture prior to positioning the subject of interest 20 within the examination space 16. As is indicated in FIG. 1, the lens 54 of the first digital camera 52 is directed downwards such that the field of view 56 of the first digital camera 52 includes a total view of the upper surface 48 of the examination table 44.

Further, the camera system 50 includes a second digital camera 58 that is identically designed to the first digital camera 52. The second digital camera 58 is installed close to an end of the examination space 16 that is distal to the entrance region 40. The second digital camera 58 is configured to take pictures of at least a region of the subject of interest 20 while the subject of interest 20 is arranged within the examination space 16 during examination. A field of view 60 of the second digital camera 58 includes a portion of the examination space 16.

The camera system control unit 62 of the camera system 50 is an integral part of the first digital camera 52, being installed in a common housing (FIG. 1). The camera system control unit 62 and the first digital camera 52 are connected by a wire-bound data link within the common housing that enables data transmission. Further, a Bluetooth® wireless data link for data transmission is established between the camera system control unit 62 and the second digital camera 58. The data to be transmitted via the data links can comprise image data as well as commands.

As will be described later in more detail, the camera system control unit 62 is configured
- to apply a computer vision algorithm to the pictures taken by the first digital camera 52 to determine at least one biometric parameter of the subject of interest 20 in relation to the upper surface 48 of the examination table 44,
- to take at least one picture with the second digital camera 58, whose field of view 60 includes a region of the subject of interest 20 that is related to the at least one determined biometric parameter,
- to use data that are at least indicative of the at least one determined biometric parameter of the subject of interest 20 to identify a subset of pixels of the at least one picture taken by the second digital camera 58 that define a region of interest 64 from which at least one physiological parameter of the subject of interest 20 is to be determined,
- to take a plurality of pictures, by the second digital camera 58, of a region of the subject of interest 20 that is related to the at least one determined biometric parameter, and
- to retrieve data from the second digital camera 58 that represent pictures of the plurality of pictures taken by the second digital camera 58, and to apply the computer vision algorithm to calculate the region of interest 64 in the pictures of the plurality of pictures for determining the at least one physiological parameter of the subject of interest 20 during examination.

In the following, an embodiment of a contact-free method of determining biometric parameters and physiological parameters of a subject of interest 20, to be examined by the magnetic resonance imaging system, is described. A flow chart of the method is given in FIG. 3. In preparation of operating the magnetic resonance imaging system, it shall be understood that all involved units and devices are in an operational state and configured as illustrated in FIG. 1.

In order to be able to carry out the method, the camera system control unit 62 comprises a software module 68 (FIG. 1). The method steps to be conducted are converted into a program code of the software module 68, wherein the program code is implemented in a digital memory unit of the camera system control unit 62 and is executable by a processor unit of the camera system control unit 62. Alternatively, the software module 68 may as well reside in and may be executable by the control unit 26 of the magnetic resonance imaging system, and data communication means are established between the camera system control unit 62 and the control unit 26 of the magnetic resonance imaging system for enabling mutual transfer of data.

It shall be understood that the magnetic resonance imaging system is in a ready-to-operate state, that the subject of interest 20 is lying in a dorsal position on the upper surface 48 of the table top 46 of the examination table 44, and that all required auxiliary devices are activated in preparation of a magnetic resonance imaging examination.

In a preparatory step 70, a region of the subject of interest to be examined is selected by an operator of the magnetic resonance imaging system via the human interface device. The region to be examined is selected to be the heart of the subject of interest 20. One biometric parameter that is related to the selected region of the subject of interest 20 would be, for instance, the position of the sternum of the subject of interest 20 relative to other natural landmarks of the subject of interest 20.

In a next step 72 of the method, prior to positioning the subject of interest 20 within the examination space 16, a picture is taken with the first digital camera 52 while the subject of interest 20 traverses the entrance region 40. The picture is a depth image including optical image data and depth values assigned to the pixels of the optical image.

In the next step 74 of the method, the camera system control unit applies a computer vision algorithm to the depth image for determining a plurality of biometric parameters of the subject of interest 20 in relation to the upper surface 48 of the examination table 44, among them the distance between the sternum and the right clavicle of the subject of interest 20. The plurality of biometric parameters is determined in relation to the foremost edge and the foremost portions of the two side edges of the upper surface 48 of the table top 46. Biometric parameters that are natural landmarks are described in terms of nearest distances to edges of the upper surface 48. The orientation of biometric parameters given by a line connecting two natural landmarks is described by a length of the line and an intersection angle between one of the edges of the upper surface 48 and an extension of the line. If any portion of the edges of the upper surface 48 is covered by the subject of interest 20, the computer vision algorithm extrapolates the visible edges by making linear connections between visible edge portions.

In an alternative approach, the camera system control unit 62 may transfer the data representing the depth image to the control unit 26 of the magnetic resonance imaging system, and the control unit 26 may apply a computer vision algorithm residing in the digital memory unit 32 of the control unit 26 and transfer results obtained with the computer vision algorithm either to the first digital camera 52 or to the second digital camera 58. The transfer of data may be enabled by a wireless data communication link such as Bluetooth®.

As an optional step 76, a plurality of parameters of a deformable human body model representing the subject of interest 20 is determined by applying a numerical fitting procedure to the data of the depth image. In this case, the exact position and orientation of the portions of the subject of interest 20 relative to the upper surface 48 of the table top 46 is determined.

Then, in a next step 78, a picture is taken by the second digital camera 58, whose field of view 60 includes a region of the subject of interest that is related to the plurality of determined biometric parameters, namely the right side of the thorax of the subject of interest.

In another step 80 of the method, the data that are indicative of the determined plurality of biometric parameters and the right side of the thorax as the region of the subject of interest 20 that is related to the determined plurality of biometric parameters are transferred to the camera system control unit 62. The camera system control unit 62 is configured to identify, in a following step 82, a subset of pixels of the picture taken by the second digital camera 58 that define a region of interest 64 from which a physiological parameter of the subject of interest 20 is to be determined, which is given by a respiration state of the subject of interest 20.

In the next step 84 of the method, the second digital camera 58 commences taking pictures of the selected region of interest. This step 84 is automatically repeated during examination of the subject of interest 20 with the magnetic resonance imaging system, and is initiated by a trigger signal that is generated and transferred to the camera system control unit 62 when the magnetic resonance imaging system commences scanning Alternatively, the step 84 may be carried out automatically upon an initial activation by an operator.

In another step 86, the camera system control unit 62 applies the computer vision algorithm to pictures of the plurality of pictures formed by the depth images taken by the second digital camera 58 for determining the physiological parameter of the subject of interest 20 during examination that is given by the respiration state, which is determined from the variance of depth information in the depth images.

While the invention has been illustrated and described in detail in the drawings and foregoing description, such illustration and description are to be considered illustrative or exemplary and not restrictive; the invention is not limited to the disclosed embodiments.

Other variations to the disclosed embodiments can be understood and effected by those skilled in the art in practicing the claimed invention, from a study of the drawings, the disclosure, and the appended claims. In the claims, the word "comprising" does not exclude other elements or steps, and the indefinite article "a" or "an" does not exclude a plurality. The mere fact that certain measures are recited in mutually different dependent claims does not indicate that a combination of these measures cannot be used to advantage. Any reference signs in the claims should not be construed as limiting the scope.

REFERENCE SYMBOL LIST

| | |
|---|---|
| 10 | medical imaging modality |
| 12 | scanning unit |
| 14 | main magnet |
| 16 | examination space |
| 18 | center axis |
| 20 | subject of interest |
| 22 | magnetic gradient coil system |
| 24 | radio frequency shield |
| 26 | control unit |
| 28 | touch screen device |
| 30 | signal processing unit |
| 32 | digital memory unit |
| 34 | radio frequency antenna device |
| 36 | radio frequency transmitter unit |
| 38 | radio frequency switching unit |
| 40 | entrance region |
| 42 | upper portion |
| 44 | examination table |
| 46 | table top |
| 48 | upper surface |
| 50 | camera system |
| 52 | first digital camera |
| 54 | lens |
| 56 | field of view |
| 58 | second digital camera |
| 60 | field of view |
| 62 | camera system control unit |
| 64 | region of interest |
| 66 | data connection |
| 68 | software module |
| 70 | step of selecting region |
| 72 | taking picture with $1^{st}$ camera |
| 74 | applying computer vision algorithm |
| 76 | determining parameter by applying fitting procedure |
| 78 | taking picture with $2^{nd}$ camera |
| 80 | transferring data to camera control unit |
| 82 | identifying region of interest |
| 84 | taking pictures with $2^{nd}$ camera |
| 86 | applying computer vision algorithm |

The invention claimed is:

1. A contact-free method of determining biometric parameters and physiological parameters of a subject of interest to be examined by a medical imaging system comprising an examination space for arranging the subject of interest within for an examination, and an examination table having an upper surface for supporting the subject of interest prior to and after the examination outside the examination space as well as while being arranged inside the examination space during the examination, the method comprising:

taking at least one first picture of the subject of interest with a first digital camera prior to arranging the subject of interest within the examination space, wherein a first field of view of the first digital camera includes a total view of an upper surface of the examination table;

determining at least one biometric parameter of the subject of interest in relation to the upper surface of the examination table using the at least one first picture taken by the first digital camera;

taking at least one second picture of the subject of interest with a second digital camera after arranging the subject of interest within the examination space, wherein a second field of view of the second digital camera includes a region of the subject of interest that is related to the at least one determined biometric parameter of the subject of interest;

identifying a subset of pixels of the at least one second picture taken by the second digital camera, using data indicative of the at least one determined biometric parameter of the subject of interest determined using the at least one first picture, that defines a region of interest from which at least one physiological parameter of the subject of interest is to be determined;

taking a plurality of pictures of the region of the subject of interest with the second digital camera; and calculating the region of interest in pictures of the plurality of pictures for determining the at least one physiological parameter of the subject of interest during the examination.

2. The method as claimed in claim 1, wherein taking the plurality of pictures of the region of the subject of interest with the second digital camera and calculating the region of interest in the pictures of the plurality of pictures for determining the at least one physiological parameter of the subject of interest is semi-automatically or automatically carried out during the examination.

3. The method as claimed in claim 1, wherein the first digital camera comprises a digital range camera, and wherein taking the at least one first picture with the first digital camera includes obtaining at least one picture that is formed as a depth image including depth data taken by the digital range camera.

4. The method as claimed in claim 3, further comprising determining a plurality of parameters of a deformable human body model representing the subject of interest by applying a numerical fitting procedure to the depth data of the depth image.

5. The method as claimed in claim 1, wherein taking the at least one second picture with the second digital camera comprises taking a plurality of depth images.

6. The method as claimed in claim 1, further comprising:
taking a plurality of pictures by at least one of the first digital camera or the second digital camera while the subject of interest is being arranged within the examination space;
tracking positions of the examination table using the plurality of pictures taken by the at least one of the first digital camera or the second digital camera; and
using data that are indicative of the tracked positions of the examination table and at least a subset of the data that is indicative of the at least one biometric parameter of the subject of interest in relation to the upper surface of the examination table for determining a position of the region of interest.

7. The method as claimed in claim 1, wherein determining the at least one biometric parameter of the subject of interest in relation to the upper surface of the examination table includes determining at least one out of an exact position and an orientation of the region of the subject of interest, of which the at least one second picture is to be taken by the second digital camera, relative to the upper surface of the examination table.

8. The method as claimed in claim 1, wherein the at least one biometric parameter comprises at least one of weight, posture or orientation of the subject of interest on the examination table.

9. The method as claimed in claim 8, wherein the at least one physiological parameter comprises a cardiac cycle parameter or a respiration cycle parameter of the subject interest.

10. A camera system for determining, in a contact-free way, biometric parameters and physiological parameters of a subject of interest to be examined by use of a medical imaging system, the medical imaging system including an examination space for arranging the subject of interest within during an examination; and an examination table having an upper surface for supporting the subject of interest prior to and after the examination outside the examination space and inside the examination space during the examination; the camera system comprising:
a first digital camera arranged in an entrance region of the medical imaging system, and configured to take at least one first picture prior to arranging the subject of interest within the examination space, wherein a field of view of the first digital camera includes a total view of the upper surface of the examination table;
a second digital camera configured to take at least one second picture of at least a region of the subject of interest while the subject of interest is arranged within the examination space during examination;
a camera system controller having at least one digital memory and at least one processor;
a data link for connecting the camera system controller, the first digital camera and the second digital camera enabling data transmission;
wherein the camera system controller is configured
to determine at least one biometric parameter of the subject of interest in relation to the upper surface of the examination table using the at least one first picture taken by the first digital camera;
to control the second digital camera to take at least one second picture, wherein a field of view of the second digital camera includes a region of the subject of interest that is related to the at least one determined biometric parameter;
to identify a subset of pixels of the at least one second picture taken by the second digital camera, using data indicative of the at least one determined biometric parameter of the subject of interest, that defines a region of interest from which at least one physiological parameter of the subject of interest is to be determined;
to further control the second digital camera to take plurality of pictures of the region of the subject of interest that is related to the at least one determined biometric parameter; and
to retrieve data from the second digital camera that represent pictures of the plurality of pictures of the region of the subject of interest taken by the second digital camera, and to calculate the region of interest in the pictures of the plurality of pictures for determining the at least one physiological parameter of the subject of interest during the examination.

11. The camera system as claimed in claim 10, wherein the camera system controller is integrated with the first digital camera or the second digital camera .

12. The camera system as claimed in claim 10, wherein at least one of the first digital camera and the second digital camera is a range camera.

13. The camera system as claimed in claim 10, wherein the at least one biometric parameter comprises at least one of weight, posture or orientation of the subject of interest on the examination table.

14. The camera system as claimed in claim 13, wherein the at least one physiological parameter comprises a cardiac cycle parameter or a respiration cycle parameter of the subject interest.

15. The camera system as claimed in claim 10, wherein the camera system controller is further configured to cause at least one of the first digital camera or the second digital camera to take a plurality of pictures while the subject of interest is being arranged within the examination space;

track positions of the examination table using the plurality of pictures taken by the at lesat one of the first digital camera or the second digital camera; and determine a position of the region of interest using data indicative of the tracked positions of the examination table and at least a subset of the data indicative of the at least one biometric parameter of the subject of interest in relation to the upper surface of the examination table.

16. A medical imaging system for acquisition of scanning data of at least a portion of a subject of interest, the medical imaging system comprising:

a scanner having an examination space for arranging at least the portion of the subject of interest within, and an entrance region for the subject of interest to enter the examination space;

a controller configured to control functions of the medical imaging system;

a signal processor that is configured to generate scanning images from the acquired scanning data; and a camera system comprising:

a first digital camera arranged in the entrance region of the scanner, and configured to take at least one first picture prior to arranging the subject of interest on an examination table within the examination space, wherein a field of view of the first digital camera includes a total view of an upper surface of the examination table;

a second digital camera configured to take at least one second picture of at least a region of the subject of interest while the subject of interest is arranged within the examination space during an examination;

a camera system controller having at least one digital memory and at least one processor;

a data link for connecting the camera system controller, the first digital camera and the second digital camera enabling data transmission;

wherein the at least one digital memory stores instructions that, when executed by the at least one processor, cause the camera system controller to:

determine at least one biometric parameter of the subject of interest in relation to the upper surface of the examination table using the at least one first picture taken by the first digital camera;

control the second digital camera to take at least one second picture, wherein a field of view of the second digital camera includes a region of the subject of interest that is related to the at least one determined biometric parameter;

identify a subset of pixels of the at least one second picture taken by the second digital camera, using data indicative of the at least one determined biometric parameter of the subject of interest, that defines a region of interest from which at least one physiological parameter of the subject of interest is to be determined;

further control the second digital camera to take plurality of pictures of the region of the subject of interest that is related to the at least one determined biometric parameter;

retrieve data from the second digital camera that represent the plurality of pictures of the region of the subject of interest taken by the second digital camera; and calculate the region of interest in the plurality of pictures for determining the at least one physiological parameter of the subject of interest during the examination.

17. The medical imaging system as claimed in claim 16, wherein the first digital camera is arranged in an upper portion of the entrance region, with a lens of the first digital camera being directed substantially downwards.

18. The medical imaging system as claimed in claim 16, wherein the medical imaging system is formed as a magnetic resonance imaging system configured for acquiring magnetic resonance images of at least a portion of a subject of interest, and wherein the scanning data are formed by magnetic resonance signals and the generated scanning images are formed by magnetic resonance images, the scanner further including a main magnet provided for generating a static magnetic field $B_o$ at least in the examination space, wherein the examination space is provided in a bore region of the main magnet;

a magnetic gradient coil system configured for generating gradient magnetic fields superimposed to the static magnetic field $B_0$;

at least one radio frequency antenna device that is configured for applying a radio frequency excitation field $B_1$ to nuclei of or within the portion of the subject of interest for magnetic resonance excitation; and at least one radio frequency antenna device that is configured for receiving magnetic resonance signals from the nuclei of or within the portion of the subject of interest that have been excited by applying the radio frequency excitation field $B_1$.

19. The medical imaging system as claimed in claim 16, wherein the first digital camera comprises a digital range camera, wherein the at least one first picture is formed as a depth image including depth data taken by the digital range camera.

20. The medical imaging system as claimed in claim 16, wherein the at least one biometric parameter comprises at least one of weight, posture or orientation of the subject of interest on the examination table, and the at least one physiological parameter comprises a cardiac cycle parameter or a respiration cycle parameter of the subject interest.

* * * * *